United States Patent [19]

Sehnem

[11] Patent Number: 4,518,791
[45] Date of Patent: May 21, 1985

[54] PREPARATION OF MENTHYL PERMETHRATE

[75] Inventor: Hans P. Sehnem, Wuppertal, Fed. Rep. of Germany

[73] Assignee: Bayer Aktiengesellschaft, Leverkusen, Fed. Rep. of Germany

[21] Appl. No.: 596,324

[22] Filed: Apr. 3, 1984

Related U.S. Application Data

[63] Continuation of Ser. No. 391,751, Jun. 24, 1982, abandoned.

[30] Foreign Application Priority Data

Jul. 14, 1981 [DE] Fed. Rep. of Germany ....... 3127752

[51] Int. Cl.$^3$ .............................................. C07C 67/02
[52] U.S. Cl. ................................................... 560/124
[58] Field of Search ........................................ 560/124

[56] References Cited

U.S. PATENT DOCUMENTS

| | | | |
|---|---|---|---|
| 3,683,005 | 8/1972 | Sota | 560/124 |
| 3,973,036 | 8/1976 | Hirano | 560/124 |
| 4,024,163 | 5/1976 | Elliott | 560/124 |
| 4,183,948 | 1/1980 | Huff | 560/124 |
| 4,345,090 | 8/1982 | Naumann | 560/124 |

FOREIGN PATENT DOCUMENTS

| | | | |
|---|---|---|---|
| 0022972 | 1/1981 | European Pat. Off. | |
| 2716771 | 11/1977 | Fed. Rep. of Germany | |
| 2843073 | 4/1979 | Fed. Rep. of Germany | |
| 2820521 | 11/1979 | Fed. Rep. of Germany | |
| 7704072 | 10/1977 | Netherlands | 560/124 |
| 2066810 | 7/1981 | United Kingdom | 560/124 |

Primary Examiner—Michael L. Shippen
Attorney, Agent, or Firm—Sprung, Horn, Kramer & Woods

[57] ABSTRACT

A process for the preparation of menthyl permethrate comprises reacting methyl permethrate or ethyl permethrate with menthol in the presence of 1 to 30 mol % of an alkali metal alcoholate, relative to the methyl or ethyl permethrate.

5 Claims, No Drawings

PREPARATION OF MENTHYL PERMETHRATE

This is a continuation of pending application Ser. No. 391,751, filed June 24, 1982, now abandoned.

The present invention relates to an unobvious process for the preparation of known menthyl permethrate.

It has already been disclosed that menthyl permethrate is obtained by heating ethyl permethrate with menthol. However, the yields obtainable in this process are not satisfactory (U.S. Ser. No. 163,361, filed 6/26/80, now pending). This is the case although the reaction is carried out using titanium tetraethylate as a trans-esterification catalyst. Titanium tetraalcohols are supposed to be particularly suitable for a trans-esterification of this type (DE-OS (German Published Specification) 2,812,365).

Trans-esterification reactions of methyl permethrate with sodium methylate as the trans-esterification catalyst are already known. However, the reaction must be carried out in a solvent in order to be able to distil off the resulting methanol. The yields and purities in the trans-esterification are not satisfactory (DE-OS (German Published Specification) 2,716,771).

The present invention now provides a process for the production of menthyl permethrate of the formula

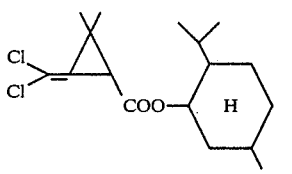

(I)

in which methyl permethrate or ethyl permethrate is reacted with menthol in the presence of 1 to 30 mol % of an alkali metal alcoholate (if appropriate in the form of an alcoholic solution thereof), relative to the methyl or ethyl permethrate.

All the enantiomers of menthyl permethrate may be produced by the process of the present invention.

It was surprising that the trans-esterification proceeds in the presence of alkali metal alcoholates without formation of the chloroacetylene compound of the formula

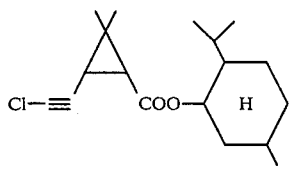

It was also surprising that it is possible, with the aid of an alkali metal alcoholate, considerably to increase the yield of the trans-esterification in comparison to the particularly effective trans-esterification catalysts, namely titanium tetraalcoholate. The increase in yield is also surprising in view of the fact that the reaction is carried out without using solvents which entrain the resulting alcohol, in the form of an azeotrope, from the reaction mixture.

The reaction according to the invention is generally carried out at a temperature between 50° and 180° C., preferably between 80° and 140° C.

Sodium methylate and sodium ethylate are preferably employed as alkali metal alcoholates. The alkali metal alcoholates are employed in an amount of 1 to 30 mol %, preferably 2 to 20 mol %, relative to the amount of methyl or ethyl permethrate employed. The alcoholates can be employed as such or in the form of their alcoholic solutions. The alcoholic solutions of the alkali metal alcoholates are preferred.

Generally 1 to 5 mols, preferably 1.1 to 2.5 mols, of menthol are employed per mol of permethrate.

Menthol is employed in the form of the d-enantiomer as well as in the form of the l-enantiomer.

The process can be carried out continuously or discontinuously.

The process is carried out without using extra solvents. This procedure has the advantage that such solvents do not have to be removed when the menthyl permethrate is separated into its optically active isomers at a later stage.

The menthyl esters obtainable by the process of the present invention may be used for separating the optical isomers of permethric acid. For this purpose, a suitable solvent is added to the resulting d-menthyl ester mixture and the d-menthyl (+)-trans-permethrate is filtered off under suction. Suitable solvents for that separation of isomers are hydrocarbons (such as ligroin, petroleum ether, hexane, heptane, pentane and cyclohexane), ketones (such as acetone, methyl ethyl ketone and methyl isobutyl ketone), esters (such as methyl- or ethylformate, methyl- or ethylacetate, methyl- or ethylpropionate), and alcohols (such as methanol and ethanol, isopropanol, n-propanol and butanol); ligroin, methanol and ethanol are particularly preferred.

Another possible method of separating the resulting menthyl ester mixture into its optically active isomers consists in carrying out the reaction without a solvent. For this purpose, the resulting ester mixture which is obtained in the form of an oil is cooled to 25°-50° C., preferably room temperature, and the sparingly soluble (+)-trans isomer which crystallizes out in the process is filtered off under suction.

The following examples illustrate processes according to the present invention.

EXAMPLE 1

223 g (1 mol) of methyl (±)-trans-permethrate, 195 g of d-menthol (1.25 mols) and 7.3 g of 11% strength sodium methylate solution (0.035 mol) were heated in a stirred flask to 110° to 120° C. under a vacuum of approximately 50 mbar. After the mixture had been further stirred for 1 hour at 110° to 120° C., stirring was continued for 1 hour at approximately 5 mbar and 110° to 120° C., excess menthol distilling off. 351 g of a pale yellow melt remained, which solidified on cooling and had a composition of 95.2% of d-menthyl (±)-trans-permethrate, 1.8% of d-menthol, 1.9% of methyl (±)-trans-permethrate and <0.2% of d-menthyl 2,2-dimethyl-3-(2-chloroethinyl)-cyclopropanecarboxylate.

When the melt was treated with a suitable solvent, the two enantiomers could be separated from each other.

EXAMPLE 2

A mixture, warmed to approximately 50° C., of 233 g of methyl (±)-trans-permethrate (1 mol), 195 g of d-menthol (1.25 mols) and 7.3 g of 11% strength sodium methylate solution (0.035 mol) was introduced over a falling-film evaporator (length of the evaporator part approximately 200 mm; φ approximately 30 mm) in the course of 1 hour, under a vacuum of approximately 5 mbar and at a heating jacket temperature of 110° C. 345.2 g of a yellowish to beige melt with a composition of 96.3% of d-menthyl (±)-trans-permethrate, 0.9% of d-menthol, 1.3% of methyl (±)-trans-permethrate and <0.2% of d-menthyl 2,2-dimethyl-3-(2-chloroethinyl)-cyclopropanecarboxylate were obtained as the bottom product.

EXAMPLE 3

223 g (1 mol) of methyl (±)-trans-permethrate, 195 g of d-menthol (1.25 mols) and 7.3 g of 11% strength sodium methylate solution (0.035 mol) were heated in a stirred flask to 100° to 120° C. under a vacuum of approximately 50 mbar. After the mixture had been further stirred for 1 hour at 110° to 120° C., stirring was continued for 1 hour at approximately 5 mbar and 110° to 120° C., excess menthol distilling off. After the addition of 500 ml of methanol, the content of the flask was cooled to 15° C., and the precipitated crystals were filtered off under suction, washed with twice 125 ml of methanol and then dried in vacuo.

143.9 g of d-menthyl (+)-trans-permethrate with a purity of 99% were obtained.

EXAMPLE 4

223 g (1 mol) of (±)-trans-permethrinic methyl ester, 312 g of d-menthol (2 mols) were initially introduced into a stirrer flask and heated to 130°–140° C.

5 g of 11% strength sodium methylate solution were added dropwise at 130°–140° C. in vacuo at 300 mbar and the mixture was then stirred for 30 minutes at 130°–140° C. and about 300 mbar, during which step methanol distilled off.

After cooling the mixture to about 60°–65° C., 500 ml of methanol were added and the reaction mixture was cooled to 5° C., (±)-trans-permethrinic acid-d-menthyl ester crystallizing out.

The crystalline product was filtered off, washed twice each time with 100 ml methanol and then dried in vacuo. 132.7 g of (±)-trans-permethrinic acid-d-menthyl ester with a content of 99.3% were obtained.

It will be appreciated that the instant specification and examples are set forth by way of illustration and not limitation, and that various modifications and changes may be made without departing from the spirit and scope of the present invention.

I claim:

1. A process for the production of menthyl permethrate of the formula

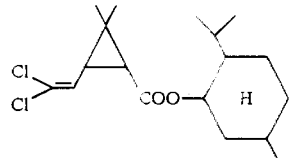

comprising reacting methyl permethrate or ethyl permethrate with menthol in the presence of about 1 to 30 mol % of an alkali metal alcoholate, relative to the methyl or ethyl permethrate, in a solvent consisting of an alcohol.

2. A process according to claim 1, wherein the reaction is carried out at a temperature between about 50° and 180° C.

3. A process according to claim 1, wherein about 2 to 20 mol % of the alkali metal alcoholate, relative to the methyl or ethyl permethrate, is used.

4. A process according to claim 1, wherein about 1.1 to 2.5 mols of menthol are used per mol of permethrate.

5. A process according to claim 2, wherein about 2 to 20 mol % of the alkali metal alcoholate and about 1.1 to 2.5 mols of menthol are used per mol of permethrate.

* * * * *